(12) United States Patent
Putz

(10) Patent No.: US 7,241,283 B2
(45) Date of Patent: Jul. 10, 2007

(54) METHOD FOR INTRACRANIAL CATHETER TREATMENT OF BRAIN TISSUE

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 76 days.

(21) Appl. No.: 10/423,587

(22) Filed: Apr. 25, 2003

(65) Prior Publication Data
US 2004/0215162 A1  Oct. 28, 2004

(51) Int. Cl.
A61M 31/00 (2006.01)

(52) U.S. Cl. ............. 604/500; 604/164.09; 604/96.01; 607/116

(58) Field of Classification Search ................ 604/500, 604/103.1, 164.09, 164, 165, 167, 93.01, 604/96.01, 158–159, 503, 506–507, 508–509, 604/103, 103.01, 171, 523, 529, 538, 378; 607/116; 600/407, 411, 424, 585
See application file for complete search history.

(56) References Cited

U.S. PATENT DOCUMENTS

| | | | |
|---|---|---|---|
| 4,346,709 A | 8/1982 | Schmitt | |
| 4,471,779 A | 9/1984 | Antoshkiw et al. | |
| 4,613,324 A * | 9/1986 | Ghajar ........................ 604/539 |
| 4,685,901 A | 8/1987 | Parks | |
| 4,777,951 A | 10/1988 | Cribier et al. | |
| 4,798,586 A | 1/1989 | Stevens | |
| 4,892,538 A | 1/1990 | Aebischer et al. | |
| 4,921,478 A | 5/1990 | Solano et al. | |
| 5,033,998 A | 7/1991 | Corday et al. | |
| 5,041,090 A | 8/1991 | Scheglov et al. | |
| 5,064,654 A | 11/1991 | Berner et al. | |
| 5,081,990 A * | 1/1992 | Deletis ........................ 600/555 |
| 5,087,244 A * | 2/1992 | Wolinsky et al. ............ 604/509 |
| 5,119,832 A * | 6/1992 | Xavier ........................ 607/117 |
| 5,154,179 A * | 10/1992 | Ratner ........................ 600/420 |
| 5,191,898 A * | 3/1993 | Millar ........................ 600/561 |
| 5,330,768 A | 7/1994 | Park et al. | |
| 5,423,877 A * | 6/1995 | Mackey ........................ 607/117 |
| 5,458,631 A * | 10/1995 | Xavier ........................ 607/117 |
| 5,505,698 A | 4/1996 | Booth et al. | |

(Continued)

Primary Examiner—Nicholas Luchessi
Assistant Examiner—Theodore J. Stigell
(74) Attorney, Agent, or Firm—Jansson Shupe & Munger Ltd.

(57) ABSTRACT

A method for intracranial treatment of a patient is disclosed. The method comprises the steps of inserting into the brain an outer catheter having an exterior surface, an inflatable balloon mounted upon the exterior surface, at least one element distal to the balloon upon the exterior surface, at least one aperture and a lumen; inflating the balloon to seal a tract created during insertion; inserting an inner catheter into the lumen which has a passageway and at least one port, the outer catheter guiding the inner catheter to the desired tissue region; and transferring fluids between the proximal end of the inner catheter and the tissue region through the passageway. Each element is adapted for monitoring or electronically stimulating brain tissue or for allowing identification of the location of the element catheter within the brain. The method facilitates regular accurate placement of the drug delivery catheter at the tissue region without additional extended brain contact during insertion. Drugs can be administered through ports near the distal end of the inner catheter or fluid can be removed from the brain through these ports.

20 Claims, 17 Drawing Sheets

U.S. PATENT DOCUMENTS

| | | |
|---|---|---|
| 5,662,607 A | 9/1997 | Booth et al. |
| 5,676,655 A * | 10/1997 | Howard et al. ............... 604/116 |
| 5,697,975 A * | 12/1997 | Howard et al. ................ 623/10 |
| 5,711,316 A * | 1/1998 | Elsberry et al. ............. 128/898 |
| 5,713,858 A * | 2/1998 | Heruth et al. ........... 604/288.02 |
| 5,728,066 A * | 3/1998 | Daneshvar ............... 604/96.01 |
| 5,782,798 A * | 7/1998 | Rise .......................... 604/500 |
| 5,792,100 A * | 8/1998 | Shantha ....................... 604/509 |
| 5,792,110 A * | 8/1998 | Cunningham ............... 604/158 |
| 5,795,331 A | 8/1998 | Cragg et al. |
| 5,807,328 A | 9/1998 | Briscoe |
| 5,810,767 A | 9/1998 | Klein |
| 5,843,022 A | 12/1998 | Willard et al. |
| 5,868,704 A | 2/1999 | Campbell et al. |
| 5,975,085 A * | 11/1999 | Rise .......................... 128/898 |
| 6,017,323 A | 1/2000 | Chee |
| 6,041,252 A | 3/2000 | Walker et al. |
| 6,096,021 A | 8/2000 | Helm et al. |
| 6,120,477 A | 9/2000 | Campbell et al. |
| 6,203,526 B1 * | 3/2001 | McBeth et al. ........... 604/96.01 |
| 6,210,346 B1 * | 4/2001 | Hall et al. .................... 600/561 |
| 6,251,115 B1 * | 6/2001 | Williams et al. ............ 606/108 |
| 6,263,225 B1 * | 7/2001 | Howard, III ................ 600/378 |
| 6,264,633 B1 | 7/2001 | Knorig |
| 6,272,370 B1 * | 8/2001 | Gillies et al. ................ 600/411 |
| 6,283,951 B1 * | 9/2001 | Flaherty et al. .............. 604/529 |
| 6,336,914 B1 * | 1/2002 | Gillespie, III .......... 604/165.01 |
| 6,510,347 B2 * | 1/2003 | Borkan ....................... 607/117 |
| 6,527,782 B2 * | 3/2003 | Hogg et al. .................. 606/130 |
| 6,629,990 B2 * | 10/2003 | Putz et al. ................... 607/113 |
| 6,656,152 B2 | 12/2003 | Putz |
| 6,733,474 B2 | 5/2004 | Kusleika |
| 6,773,447 B2 | 8/2004 | Laguna |
| 6,832,115 B2 * | 12/2004 | Borkan ........................ 607/117 |
| 6,887,229 B1 * | 5/2005 | Kurth ......................... 604/525 |

* cited by examiner

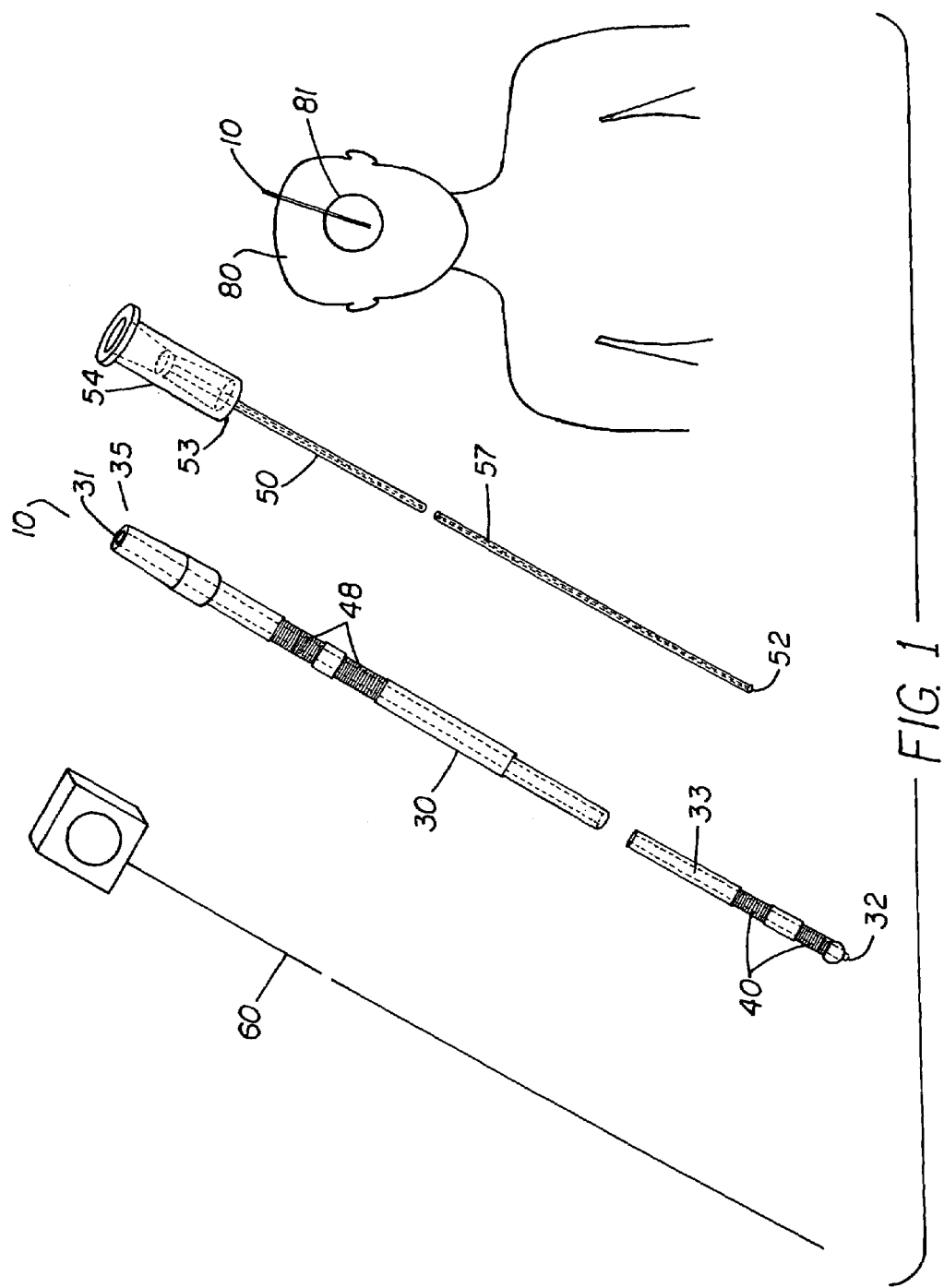

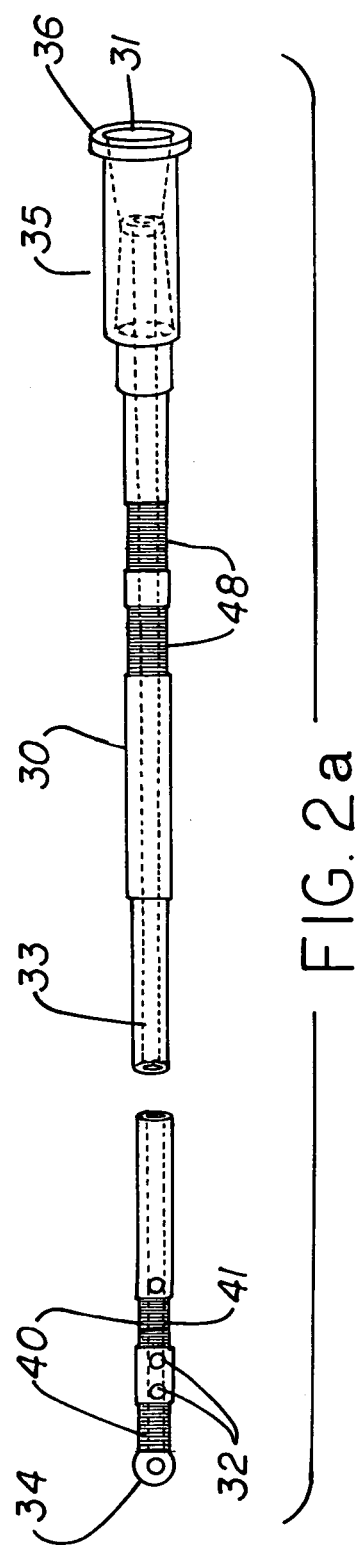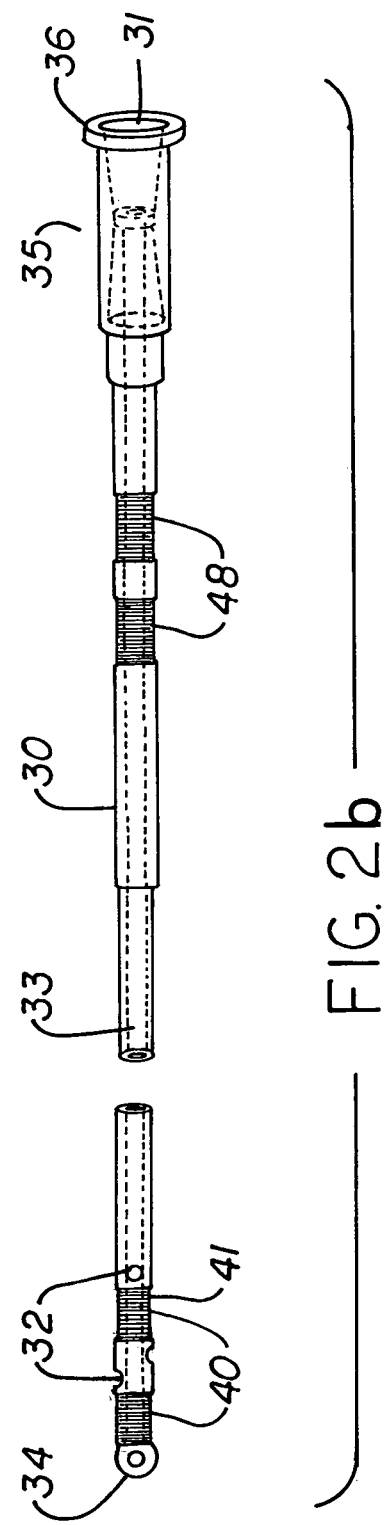

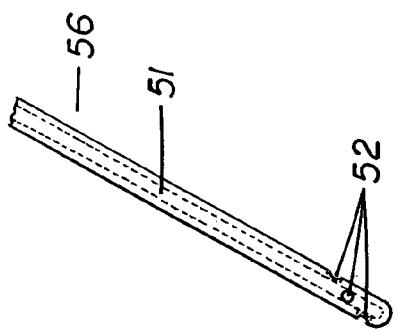
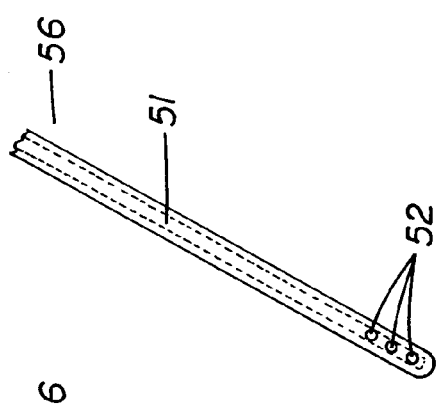
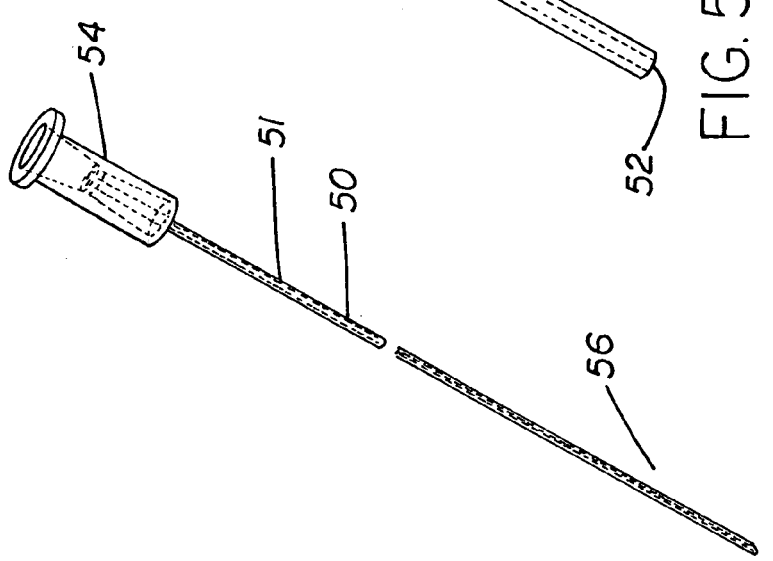

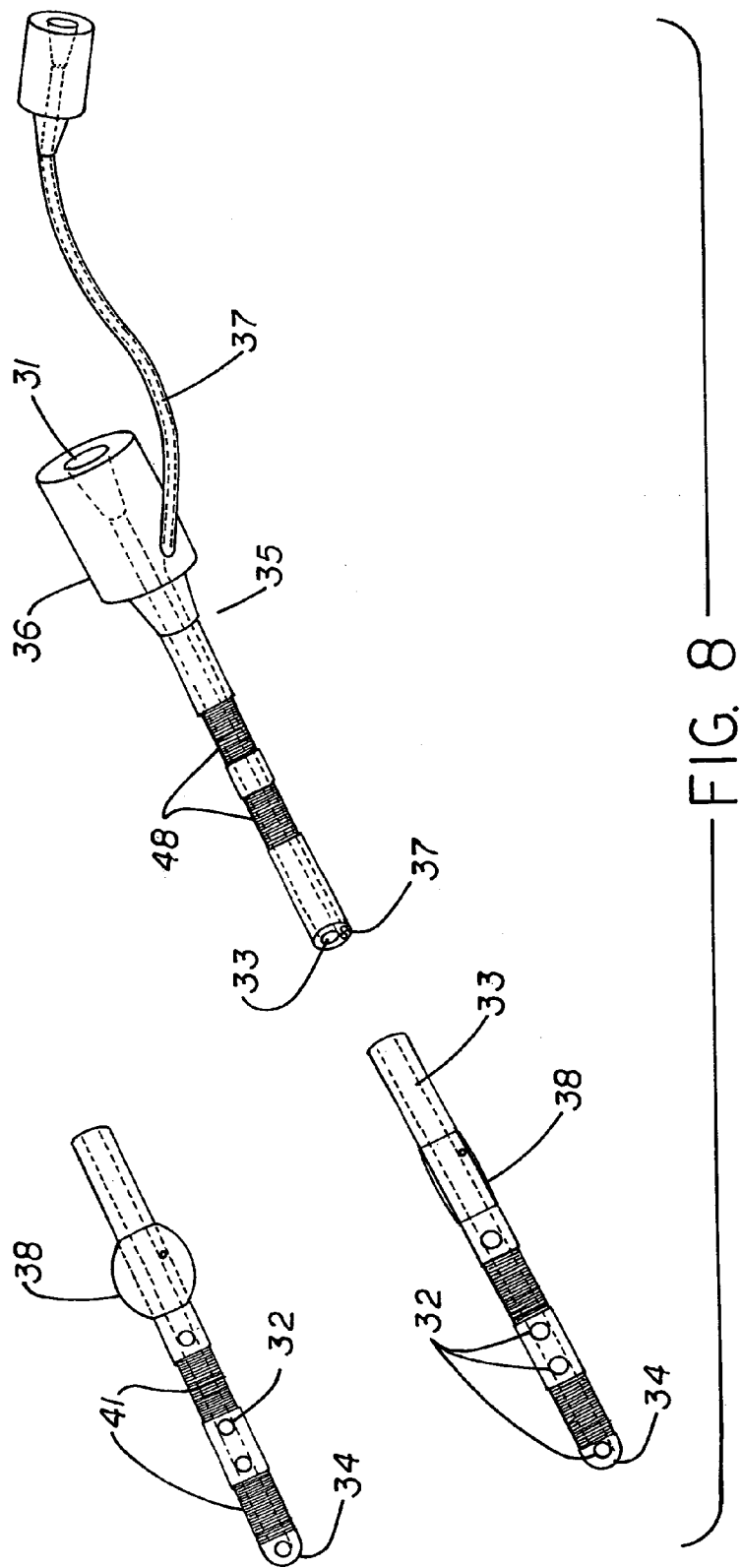

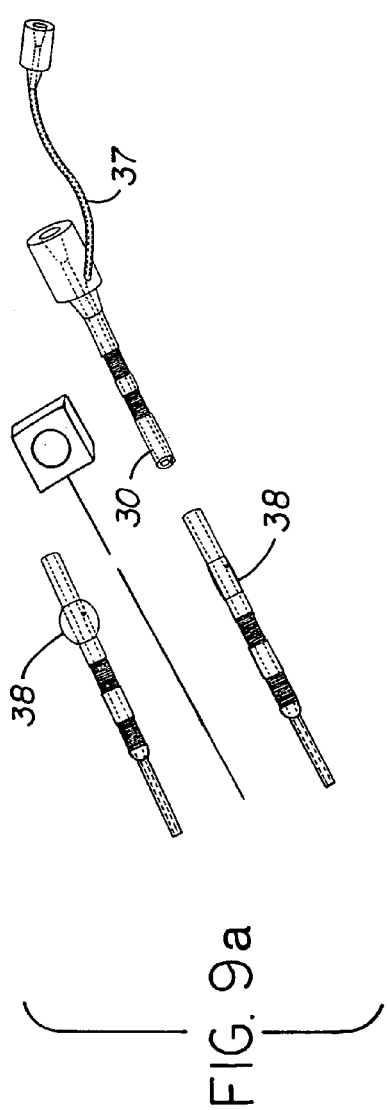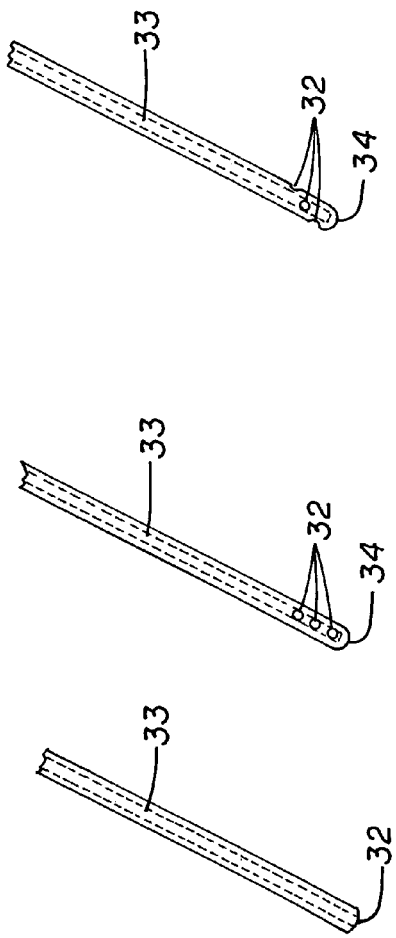

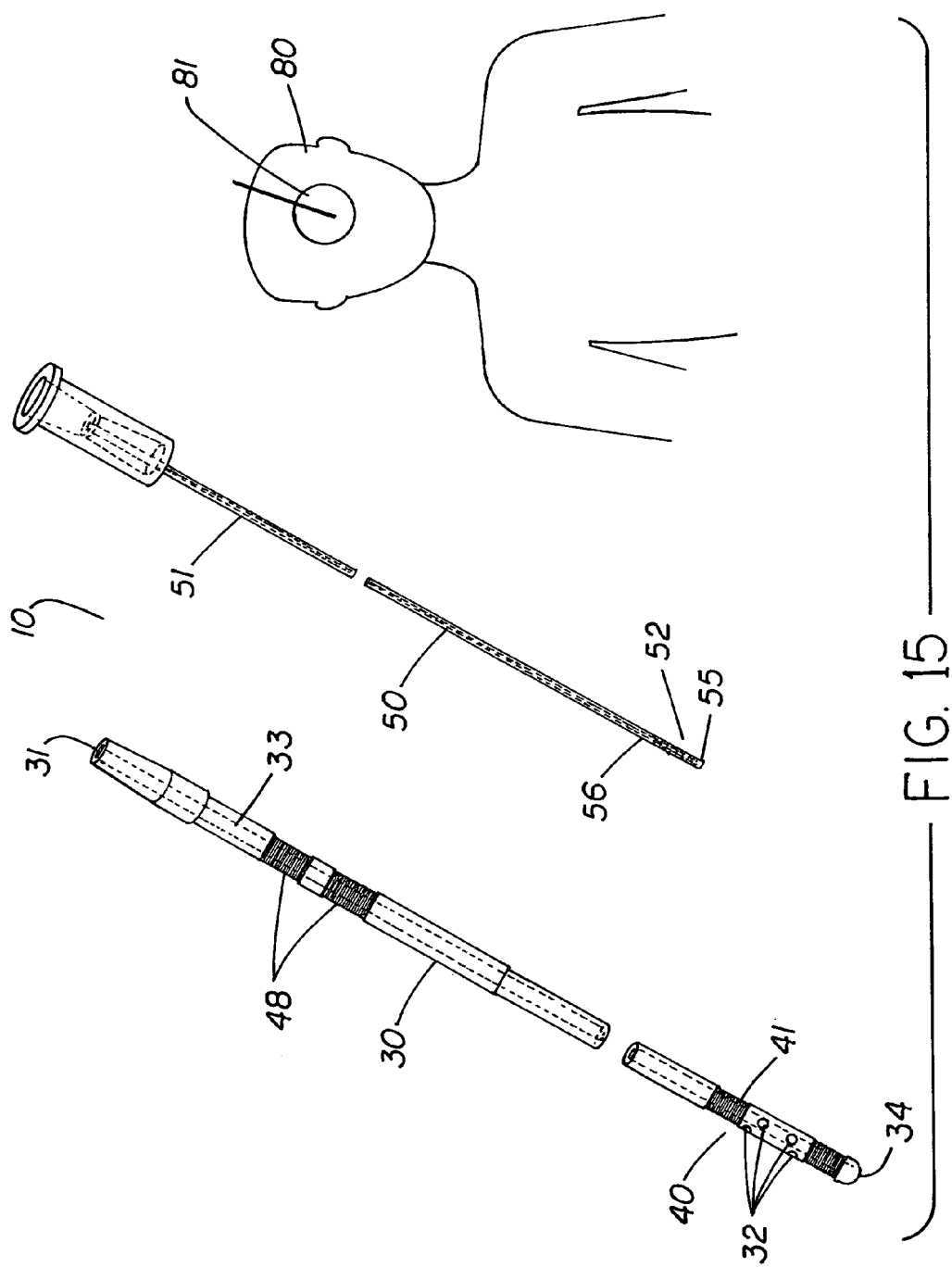

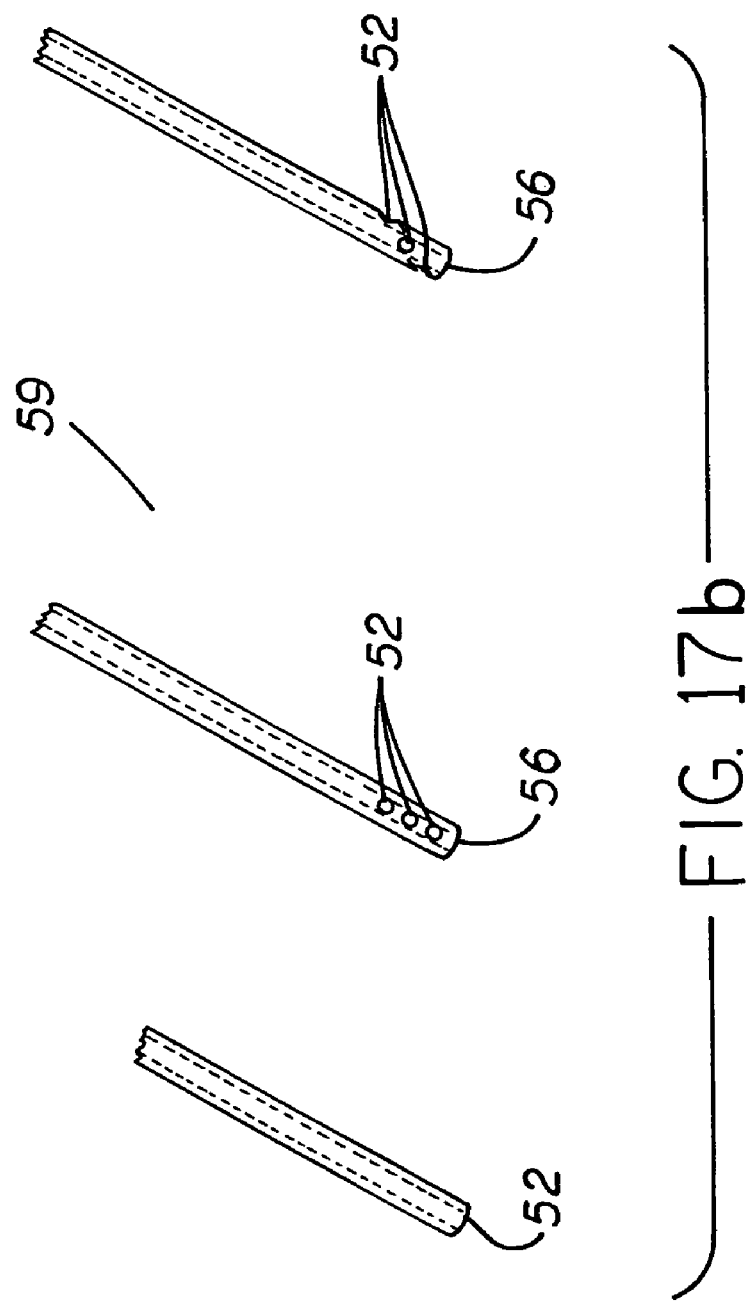

METHOD FOR INTRACRANIAL CATHETER TREATMENT OF BRAIN TISSUE

FIELD OF INVENTION

The present invention relates to the intracranial transfer of fluids and, in particular, to devices for affecting such transfer.

BACKGROUND OF THE INVENTION

Movement disorders such as epilepsy and Parkinson's disease have been estimated to affect some 1–2% of the developed world's population and up to 10% of people in underdeveloped countries. Currently, approximately 75% of those who suffer from movement disorders are responsive in some degree to drugs.

Electrical stimulation has also been utilized to treat some movement disorders. In the treatment of epilepsy, studies have been performed in which awake patients undergoing temporal lobe surgery underwent cortical stimulation. Such stimulation of the visual and hearing areas of the brain reproducibly caused the patients to experience visual and auditory phenomena. This discovery was made possible by the identification that certain brain subregions served specific functions, such as sight, hearing, touch and movement of the extremities and proved that direct electrical stimulation of the brain regions could cause partial reproduction or suppression of the functions.

As suggested by these results, it is known that certain types of treatment of specific portions of the brain are able to suppress certain unwanted behavior which results from movement disorders. This behavior may include seizures such as those suffered by epileptics. However, the studies faced a major problem in that there was an inability to precisely electrically stimulate very small volumes of the brain.

The advent of needle-shaped penetrating depth electrodes helped to overcome this obstacle faced by electrical stimulation. Depth electrodes can be placed within the brain tissue itself, enabling optimal surface contact with elements of the brain that are targeted for stimulation. This allowed for safe, chronic electrical stimulation of very small discrete volumes of brain.

In treatment, electrical stimulation has been used with the recording and analysis of changes in brain activity to predict the occurrence of epileptic seizures. The time of onset of such seizures is often predictable by neural discharge monitoring, even when the exact causal nature of precipitating dysfunction is not understood. Electrodes have been used to obtain signals representative of current brain activity along with a signal processor for continuous monitoring and analysis of these electrical signals in order to identify important changes or the appearance of precursors predictive of an impending change.

While the electrical stimulation of brain tissue has been somewhat effective in the treatment of migraines, epilepsy and other neurological problems, patients often experience diminishing returns with such treatment. Furthermore, because each patient reacts differently to electrical stimulation, substantial time must be spent to determine the specific amplitude, frequency, pulse width, stimulation duration, etc. which may result in effective treatment. In addition, such parameters often require continual adjustment in order to remain effective.

The combination of drug delivery and electrical stimulation and/or monitoring has been shown to be more effective in some intracranial treatments. Such drug delivery and stimulation or monitoring is typically performed by instruments which are inserted into the brain at different locations or along different tracks. Other systems employ a single device which must be removed and reinserted to provide for delivery of multiple drugs or use of different electrical devices.

Since the introduction of probes or other similar devices into the brain is common in many surgical procedures today, there are a variety of probes available. Such probes typically include ports for drug delivery or electrical, chemical, electrochemical, temperature and/or pressure contacts which enable the observation and analysis of the brain state or contacts providing stimulation. These ports and contacts must typically be positioned at specific points or regions in the brain.

Probes used in intracranial penetration are typically fabricated so that their introduction to the brain is as minimally traumatic as possible. In addition to being minimally traumatic during insertion, certain inserted probes must also be able to remain implanted without causing injury through unintended movement. In some uses, a probe may be implanted and remain in the patient's brain for weeks or longer. Changes in the positioning of the probe often occur during placement or during such extended periods. Therefore, the probe must be capable of precise placement and as biocompatible as possible. In response to these requirements, state of the art intracranial probes are typically thin, flexible pieces with smooth surfaces to minimize the amount of brain tissue contacted and to minimize damage to contacted brain tissue.

While such thin, flexible probes are sufficiently biocompatible, they are delicate and often difficult to insert along specific trajectories or lines of insertion. During typical implantation, a surgeon feeds the probe into the brain through an aperture in the skull. In this process, the surgeon has very little control over the distal end of the probe. In order to provide more rigidity to the probe to overcome this problem, a removable stylet may be inserted into the probe before implantation. Still, veering from the intended line of insertion is not altogether prevented by introduction of a stylet to the probe.

While typical intracranial probes have smooth surfaces so as to not cut any contacted tissue, many such probes are made of elastomers or other such materials which, although smooth, do not easily slide through brain tissue. The drag encountered by these types of probes can result in injury to the contacted brain tissue.

Therefore, there is a continuing significant need in the field of intracranial treatment, particularly with insertion of probes into the interior of the brain, for improvements in accuracy of insertion and avoidance of injury, while retaining efficiency and ease of use.

In addition, there is a need in the field of intracranial treatment to minimize the invasiveness of intracranial treatment and to reduce the number of instruments which penetrate brain tissue or the number of times a single instrument must penetrate brain tissue.

Furthermore, there is a need in the field of intracranial treatment to provide the ability to precisely locate the position of a probe during insertion to ensure proper positioning.

OBJECTS OF THE INVENTION

It is an object of the invention to provide an improved intracranial insertion device which prevents injury to the patient.

Another object of the invention is to provide a catheter assembly which is simple in structure and operation in order to facilitate intracranial procedures.

Another object of the invention is to provide a catheter assembly which allows for the precise insertion of drug delivery ports or contacts in the brain while avoiding extensive trauma to and scarring of brain tissue.

Another object of the invention is to provide an outer catheter which includes contacts for stimulation and/or monitoring the brain and which receives and guides a drug delivery catheter to the targeted brain tissue for drug delivery.

Another object of the invention is to provide an outer catheter which includes contacts for stimulation and/or monitoring the brain and which receives and guides a cerebral spinal fluid recovery catheter to the targeted brain tissue for sampling cerebral spinal fluid through a dialysis membrane.

Another object of the invention is to provide an outer catheter which includes location markers for allowing the positioning of the outer catheter to be determined during or after insertion of the catheter into the brain and which receives and guides an inner catheter for delivering or removing fluid from the targeted brain tissue.

Another object of the invention is to provide a depth electrode which receives and guides an inner catheter for delivering or removing fluid from the targeted brain tissue and remains in position when the inner catheter is removed, allowing for further insertions of the inner catheter without further extended contact with brain tissue during insertion.

Another object of the invention is to provide an outer catheter including an inflatable balloon for sealing any insertion tract to permit effective drug delivery to the targeted brain tissue region.

Still another object of the invention is to provide a method of safely inserting, through use of an outer catheter, a catheter in a patient's brain which provides for drug delivery and/or cerebral spinal fluid withdrawal as well as stimulation and/or monitoring of brain activity.

Yet another object of the invention is to provide a trajectory catheter which can be mounted to the patient's skull and connected to an inner catheter such that the inner catheter is positioned and held at the targeted brain tissue region.

These and other objects of the invention will be apparent from the following descriptions and from the drawings.

BRIEF SUMMARY OF THE INVENTION

In accordance with the present invention, an intracranial catheter assembly is provided for precise treatment of brain tissue. The catheter assembly of this invention overcomes certain problems and shortcomings of the prior art, including those noted above, and provides a unique structure satisfying a number of specific intracranial treatment needs.

The catheter assembly comprises (a) an outer catheter having a proximal opening, at least one aperture and a lumen connecting the opening and the at least one aperture, and at least one element; and (b) an inner catheter adapted to be received within the lumen and including a passageway and at least one port for delivering fluids to a tissue region within the patient's brain. In preferred embodiments the assembly further comprises a rigid stylet received within the lumen for insertion into the patient's brain (since the preferred outer catheter is flexible) and removed before insertion of the inner catheter into the lumen.

In certain embodiments, the aperture is preferably axially aligned with the inner lumen. In such embodiments, the inner catheter can extend through the aperture when the inner catheter is received within the lumen.

In other embodiments, the outer catheter has a closed end which blocks passage of the inner catheter therethrough. In such embodiments the aperture is located along a side of the outer catheter. The outer catheter can include more than one aperture which are preferably radially and axially spaced about the outer catheter. In still other embodiments, the outer catheter has an aperture axially aligned with the inner lumen and other apertures which are located along a side which may be radially or axially spaced.

In certain preferred embodiments, the outer catheter further includes a conduit extending from the proximal end to an inflatable balloon which is adapted to be inflated to seal a tract created during insertion of the assembly into the brain. The inflatable balloon may be inflated with a fluid which does not come in contact with brain tissue; however, in some embodiments, the balloon is inflated with a fluid which is then introduced to the tissue region surrounding the balloon. Such a fluid can be any type of medicament, and will be referred to herein as a "drug," such term including other types of medicaments. Introduction of the fluid can occur at a slow or fast rate as fluid permeates through or otherwise leaves the balloon and can occur before, simultaneous with, or after transfer of fluid through the lumen or passageway such that multiple fluids may be administered separately through the catheter assembly.

The inner catheter preferably has at least one port. In some embodiments, the ports are designed to be in communication with the apertures of the outer catheter when the inner catheter is inserted into the lumen to a preferred position. In other embodiments, the position of the ports do not correspond with the apertures—particularly when an aperture is axially aligned with the lumen and the distal portion of inner catheter passes through the aperture. In certain preferred embodiments there are at least two ports which are axially spaced on a side of the inner catheter along a line parallel to the passageway. In other embodiments, the ports are radially and axially spaced about the inner catheter. In yet other embodiments, the inner catheter includes a port axially aligned with passageway and at least one port positioned on its side.

The preferred port is adapted to deliver or remove fluids from the surrounding brain tissue. In certain embodiments, the port includes a dialysis membrane adapted to receive cerebral spinal fluid.

In some embodiments, the outer catheter and inner catheter preferably have proximal ends with one of the proximal ends including a luer fitting and the other of the proximal ends configured for connection to the luer fitting. In such embodiments, the outer catheter is inserted into the patient's brain to a desired position, then the inner catheter is inserted into the lumen and the catheters are connected to one another via the luer fitting such that the inner catheter is secured at the desired position in the brain.

In some embodiments, the outer catheter is preferably adapted to connect to the patient's skull when inserted to the targeted portion. In such embodiments, the inner catheter is preferably adapted to connect to the outer catheter when inserted to the targeted portion. Therefore, during use, the outer catheter may be inserted to the targeted position and secured to the skull while the inner catheter is inserted into the lumen and then secured to the outer catheter. Such connections are preferably performed by screwing the outer catheter to the skull and the inner catheter to the outer catheter, i.e., via threads on each of the catheters.

In certain embodiments, the at least one element is a contact which monitors activity in the brain. In such embodiments, the outer catheter can be considered as a depth electrode. The contact may be of the type which senses electrical, chemical or electrochemical activity in the brain. The contact preferably senses brain function in the tissue region. In other embodiments the contact provides electrical stimulation to the tissue region. The contact may be a collar circumscribing the outer catheter, a micro contact, a macro contact, or other types of contacts. The depth electrode preferably includes an electrical lead corresponding to each contact.

In other preferred embodiments, the element is a location marker for allowing the position of the outer catheter to be located within the brain. The location marker is preferably adapted to be located by magnetic resonance imaging or computerized x-ray tomography such that such imaging devices can be used to locate the position of the catheter in the patient's brain during or after insertion or implantation.

In yet other preferred embodiments, multiple elements on the outer catheter include both at least one contact and at least one marker.

The invention also includes a method of treating a tissue region in the brain of a patient comprising (a) inserting into the brain an outer catheter having at least one element, at least one aperture and a lumen, (b) inserting into the lumen an inner catheter having a passageway extending between a proximal end and at least one port, and (c) transferring fluids between the tissue region and the proximal end through the passageway. In the inventive method the outer catheter guides the inner catheter to the tissue region. Therefore, the inner catheter may be non-rigid or otherwise ill-designed to be precisely inserted into a patient's brain and still be precisely positioned at the desired position in the brain. The method preferably includes positioning a stylet in the lumen during insertion of the outer catheter into the brain and removing the stylet from the outer catheter before the inner catheter is inserted into the lumen. The method also preferably includes connecting the outer catheter to the patient's skull and connecting the inner catheter to the outer catheter. The catheters may be connected by screwing reciprocal threaded parts together, by use of a luer fitting or other connecting members.

In certain embodiments, the element is a location marker and the method further includes locating the position of the location marker in the brain. The location marker is preferably located by magnetic resonance imaging or by computerized x-ray tomography.

In other embodiments, the element is a contact and the method further comprises monitoring the tissue region via the contact. The contact preferably provides electrical stimulation to the tissue region, senses brain activity in the tissue region, or multiple contacts allow for performance of each of these functions. The preferred monitoring action includes sensing chemical changes at the tissue region and/or sensing electrical changes at the tissue region. The contact is preferably a collar-type contact, a micro contact for monitoring cells or neurons, a macro contact for monitoring tissue, or a fiber optic contact.

In preferred methods, the inner catheter has a distal end which passes through the aperture into the tissue region beyond the outer catheter during the insertion of the inner catheter into the lumen. In other preferred embodiments, the inner catheter has a distal end and the outer catheter has a closed lumen so that the distal end is contained within the outer catheter when the inner catheter is inserted into the lumen.

The transferring action preferably includes delivering drugs to the tissue region through the at least one port and/or withdrawing cerebral spinal fluid through the at least one port. In certain embodiments, the inner catheter includes a micro-dialysis membrane at the at least one port and cerebral spinal fluid passes through the membrane during the withdrawing action.

In certain preferred embodiments, the outer catheter includes an inflatable balloon and the method further comprises inflating the balloon to seal a tract created during insertion of the assembly into the brain. The balloon is preferably inflated with a drug which is delivered to the tissue region through the balloon. The preferred method further comprises delivering a second drug to the tissue region through the at least one port.

Some preferred embodiments of the invention include a first inner catheter having a first length for delivering fluids to a first tissue region and a second inner catheter having a second length greater than the first length for delivering fluids to a second tissue region within the patient's brain. More preferably, the assembly comprises a third inner catheter having a third length greater than the second length for delivering fluids to a third tissue region within the patient's brain. As is understood the assembly can include many inner catheters of different lengths and having different arrangements of ports to provide for treatment of specific desired tissue regions in the brain.

Each different inner catheter is preferably introduced to the brain through a single outer catheter such that an instrument penetrates a large portion of the brain tissue between the skull and the desired tissue regions only once. Such an assembly allows for inserting the outer catheter through the intervening brain tissue, precisely locating the outer catheter relative to a specific tissue region, inserting corresponding inner catheter (the inner catheter which would position a port at the tissue region when inserted into the lumen) in the lumen, treating the tissue region, withdrawing the used inner catheter from the lumen, inserting another inner catheter corresponding to another desired specific tissue region, treating that region, etc.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment. In the drawings:

FIG. 1 is a perspective view of a catheter assembly and patient, shown with dashed lines representing otherwise unseen internal features, in accordance with the invention.

FIGS. 2a and 2b are perspective views of an alternate outer catheter having a closed end, shown with dashed lines representing otherwise unseen internal features, in accordance with the invention.

FIGS. 5*a*, 5*b*, 5*c* and 5*d* are perspective views of alternate inner catheters, shown with dashed lines representing otherwise unseen internal features, in accordance with the invention.

FIG. 8 is a perspective view of an alternate version of the outer catheter shown in FIGS. 6 and 7, shown with dashed lines representing otherwise unseen internal features, in accordance with the invention.

FIGS. 9*a*, 9*b*, 9*c* and 9*d* are perspective views of alternate versions of the outer catheters shown in FIGS. 6–8, shown with dashed lines representing otherwise unseen internal features, in accordance with the invention.

FIGS. 15 and 16 are perspective views of a preferred catheter assembly in which the inner catheter includes a dialysis membrane, shown with dashed lines representing otherwise unseen internal features, in accordance with the invention.

FIGS. 17*a* and 17*b* are perspective views of a preferred catheter assembly which provides for connection between the outer catheter and the patient's skull and includes a location marker and including a set of inner catheters, shown with dashed lines representing otherwise unseen internal features, in accordance with the invention.

DETAILED DESCRIPTION OF PREFERRED EMBODIMENTS

Figures 3, 4:
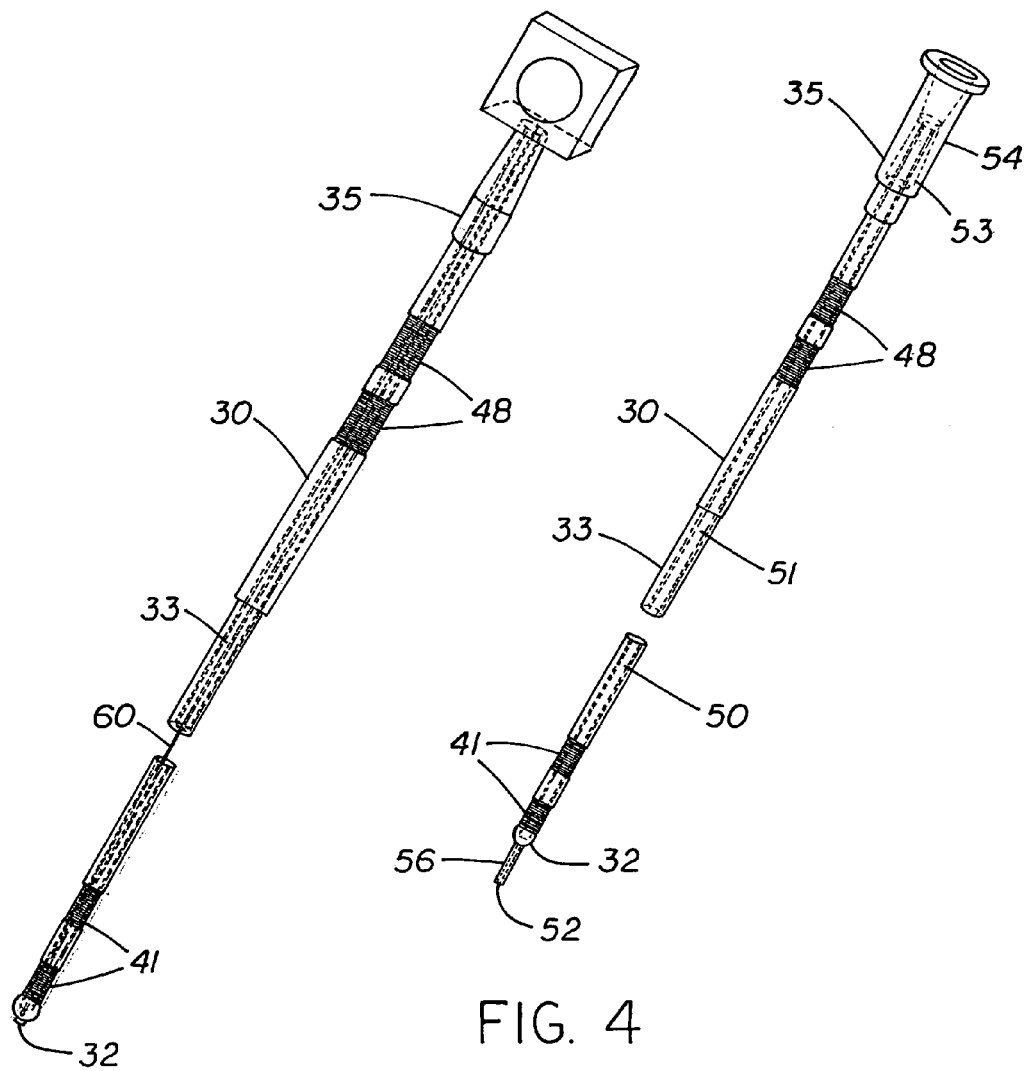
FIG. 3 is a perspective view of an outer catheter when receiving a stylet, shown with dashed lines representing otherwise unseen internal features, in accordance with the invention.
FIG. 4 is a perspective view of an outer catheter when receiving an inner catheter, shown with dashed lines representing otherwise unseen internal features, in accordance with the invention.

Referring to FIG. 1, a catheter assembly in accordance with the present invention is generally designated by the reference numeral 10. Catheter assembly 10 allows intracranial treatment of a patient by providing an outer catheter 30 and inner catheter 50 which cooperate to transfer fluids between a tissue region 81 in the patient's brain 80 and an external receptacle or device. Also shown with catheter assembly 10 is stylet 60 which can be received by outer catheter 30 to prevent the entrance of brain tissue into outer catheter 30 during insertion into the brain.

Outer catheter 30 is preferably between about 0.6 and 1.5 millimeters, most preferably about 1.0 millimeter and is comprised of polyurethane, silicone, polyimede, or other biocompatible material. Outer catheter 30 includes a lumen 33 which extends from proximal opening 31 to aperture 32. Outer catheter 30 also includes elements 40 which may provide for monitoring of brain tissue or for providing a location marker for determining the precise position of outer catheter 30 within the brain. As shown, elements 40 include distal contacts 41 which can sense brain activity in tissue region 81 via electrical, electrochemical, chemical or pressure changes within the brain. Preferred contacts 41 are platinum, platinum iridium or other biocompatible conductive material. For pressure sensing, contact 41 is a miniature pressure-sensing contact which is preferably a miniature optical pressure transducer less than about 2 millimeters long as discussed in U.S. patent application Ser. No. 09/948,153, filed Sep. 6, 2001 and incorporated herein by reference. Brain activity sensed by distal contacts 41 is transmitted to an external connector through proximal contacts 48 and then to a computer or instrument which records and/or analyzes such activity. During insertion or implantation proximal contacts 48 remain outside of the patient and allow for connection to such an instrument. Proximal contacts 48 are preferably stainless steel or other alloys or materials which are noncorrosive conductors which can endure the sterilization process.

Inner catheter 50 is preferably polyimede, polyimede-coated glass or other similar material and includes a passageway 51 which extends from proximal end 53 to port 52. Passageway 51 has an inner diameter which may vary depending on the desired flow rate of fluid therethrough but is preferably between about 25 microns and 0.5 millimeters. As shown, port 52 is axially aligned with passageway 51 (as is aperture 32 with lumen 33) such that fluids may be transferred to or from the tissue region 81 at port 52, e.g, drugs may be administered to tissue region 81, cerebral spinal fluid may be withdrawn, or both. Inner catheter 50 is shown as including a luer fitting 54 which provides for connection with outer catheter 30.

FIGS. 2*a* and 2*b* depict alternate embodiments of outer catheter 30 in which lumen 33 has a closed end 34. In such embodiments, apertures 32 are positioned along the side or sides of the outer catheter. For instance, FIG. 2*a* shows apertures 32 axially spaced along a line parallel to lumen 33. FIG. 2*b* shows apertures 32 axially and radially spaced about outer catheter 30. In addition, outer catheter 30 is shown as including a luer fitting 36 providing for connection with inner catheter 50.

FIG. 3 shows stylet 60 received within lumen 33 for insertion into the patient's brain. Stylet 60 prevents brain tissue from entering lumen 33 during insertion and may provide rigidity to outer catheter 30 if outer catheter 30 is not rigid.

FIG. 4 shows inner catheter 50 received within lumen 33. As shown, distal portion 56 of inner catheter 50 extends through aperture 32 to reach the desired region in the brain. Port 52 is shown axially aligned with passageway 51 although additional ports 52 can be positioned along the sides of distal portion 56.

FIG. 5*a* shows inner catheter 50 while FIGS. 5*b*, 5*c* and 5*d* show alternate embodiments of distal end 56 of inner catheter 50 in which port 52 is axially aligned with passageway 51 (FIG. 5*b*), multiple ports 52 are axially spaced along a line parallel to passageway 51 (FIG. 5*c*), and multiple ports 52 are axially and radially spaced about inner catheter 50 (FIG. 5*d*). It is understood that an inner catheter 50 can include both an axially aligned port 52 and ports 52 positioned along its side.

Figure 6:
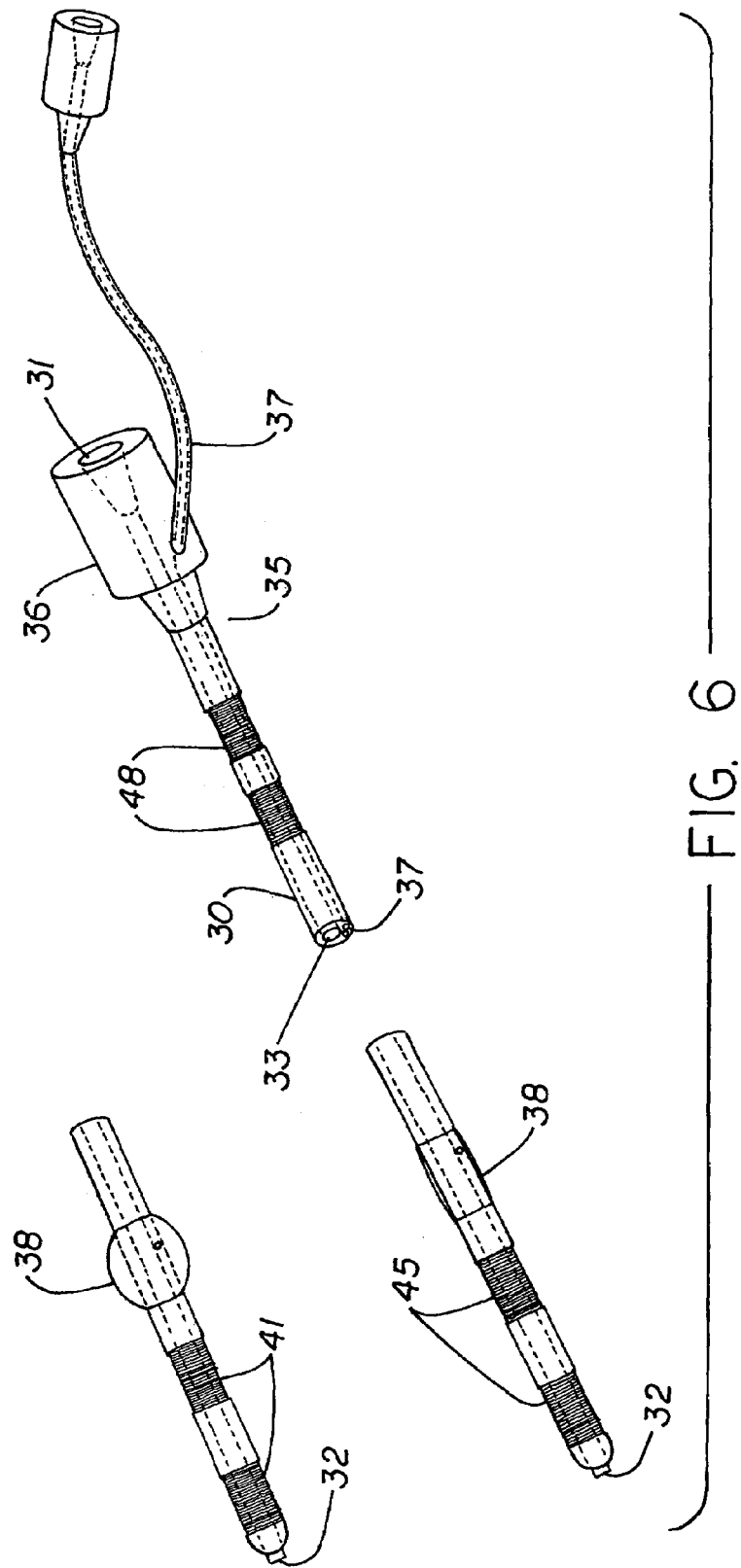
FIG. 6 is a perspective view of an outer catheter having a balloon shown both deflated and inflated, with dashed lines representing otherwise unseen internal features, in accordance with the invention.
Figure 7:
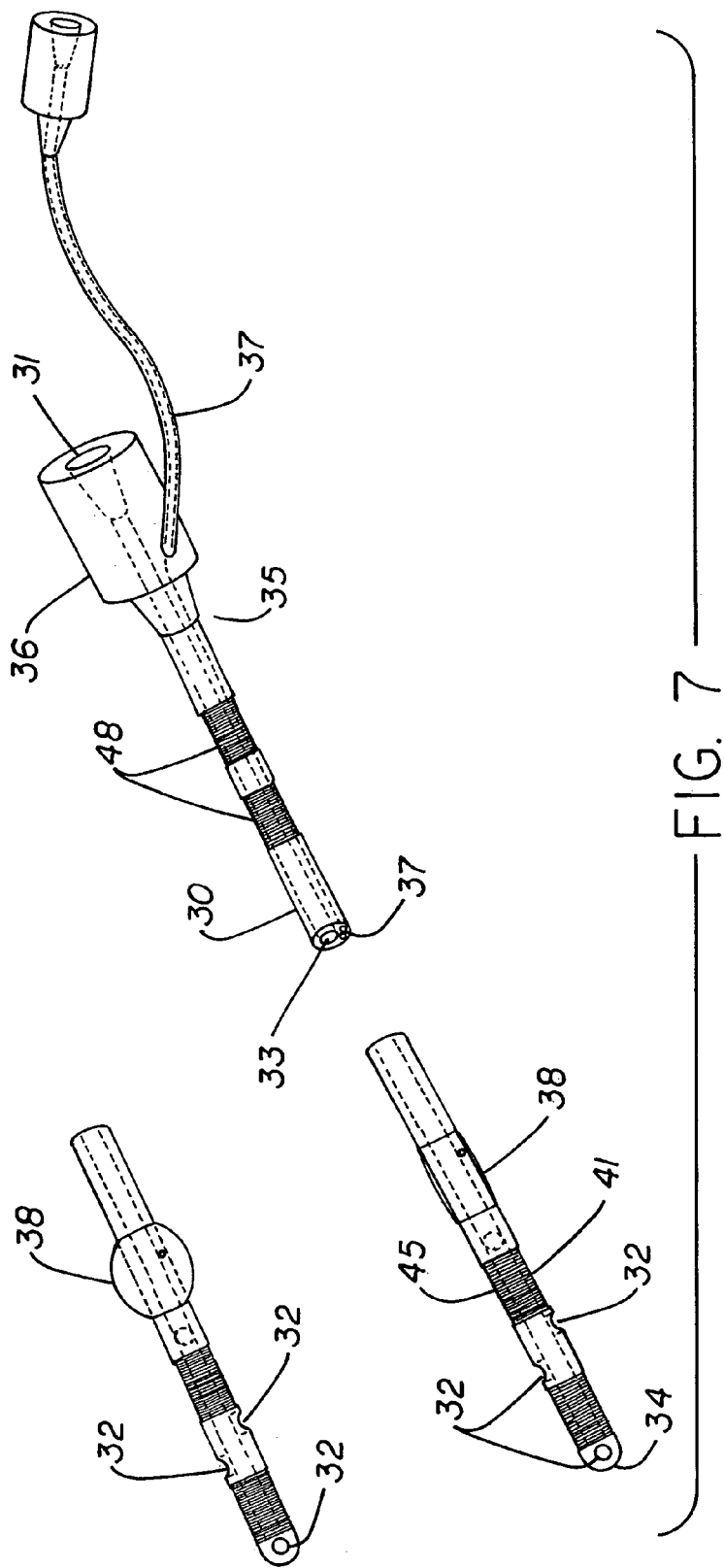
FIG. 7 is a perspective view of an alternate version of the outer catheter shown in FIG. 6, shown with dashed lines representing otherwise unseen internal features, in accordance with the invention.
Figure 10:
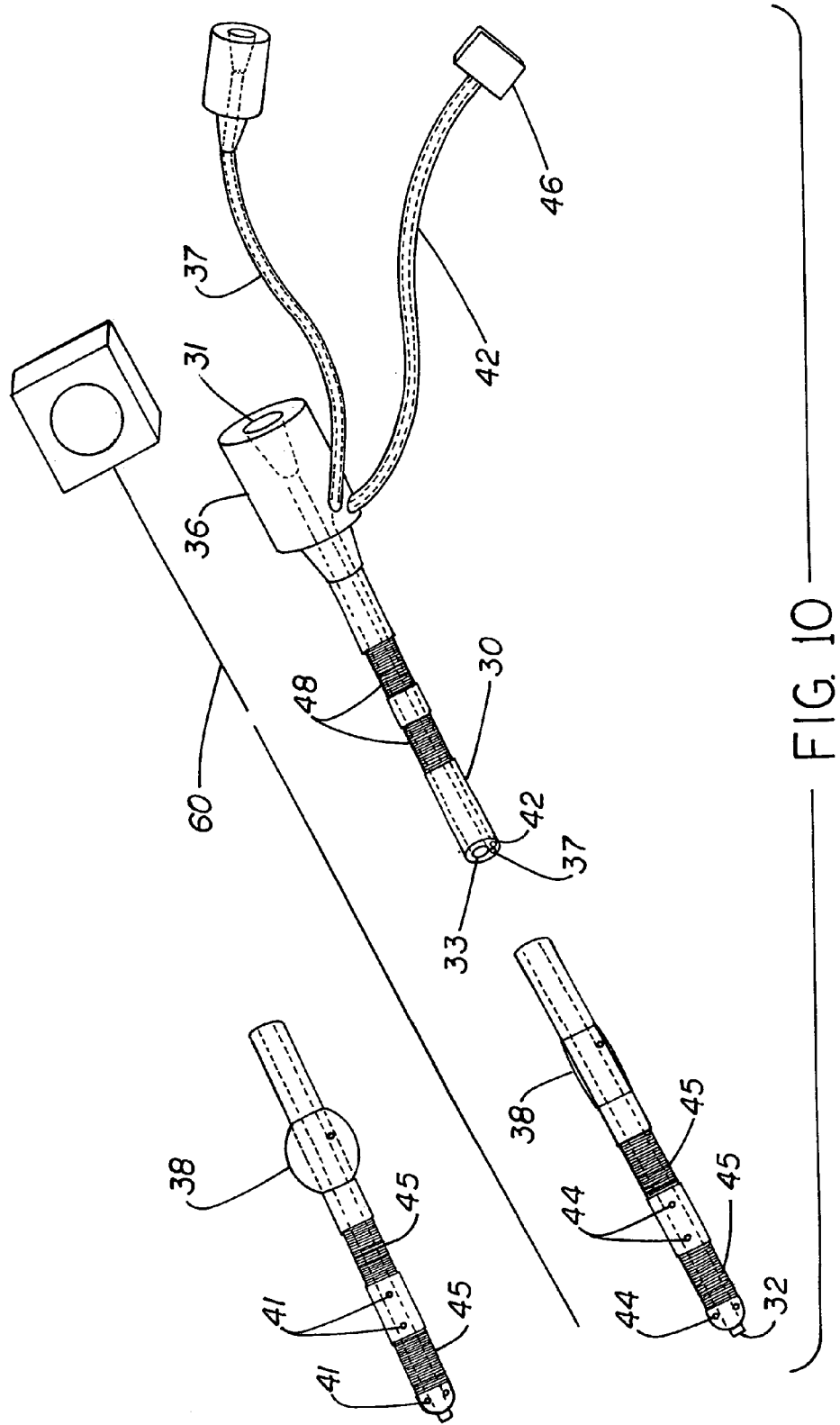
FIG. 10 is a perspective view of a preferred outer catheter having a balloon and contacts with an electrical lead, shown with dashed lines representing otherwise unseen internal features, in accordance with the invention.
Figure 11:
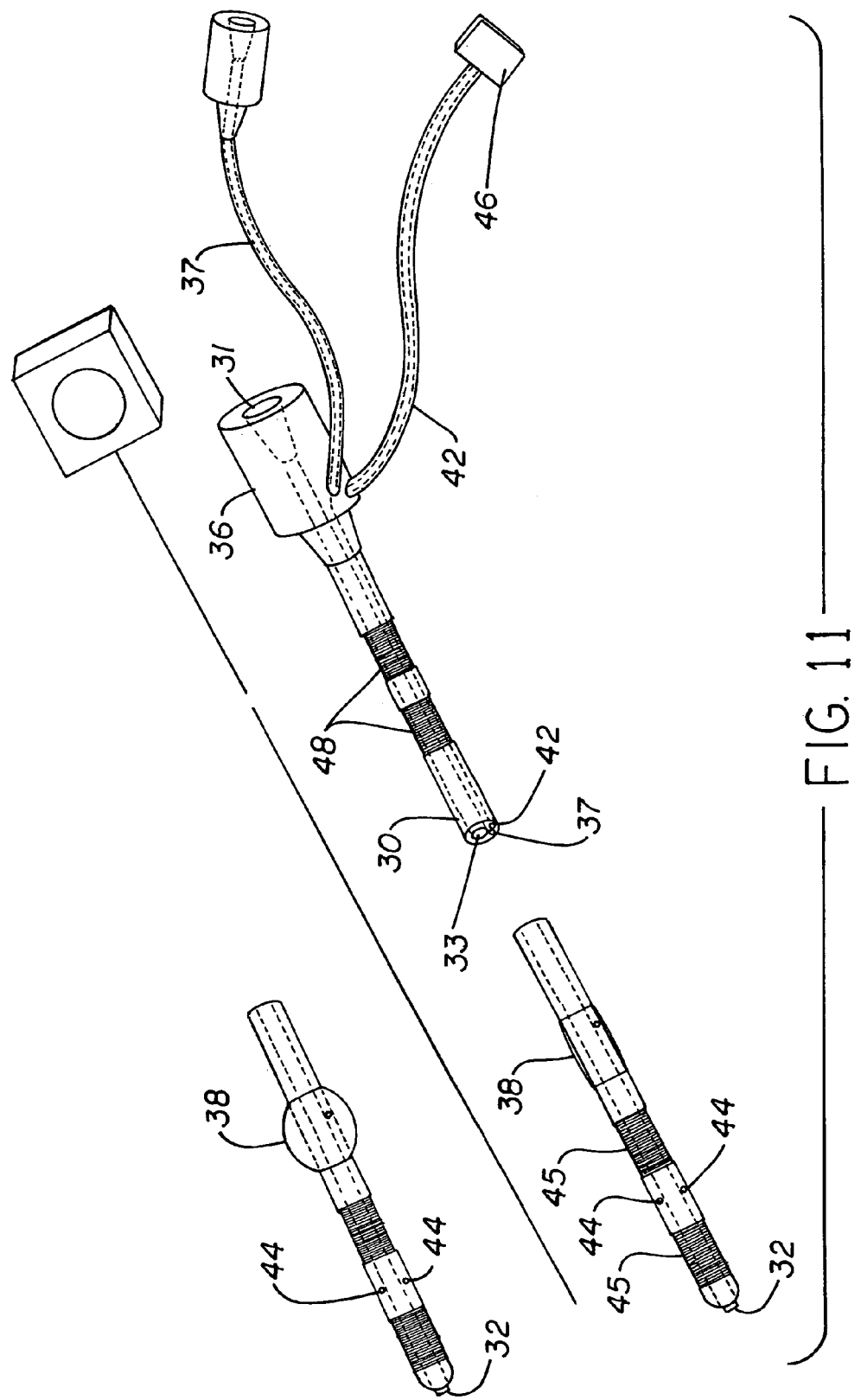
FIG. 11 is a perspective view of an alternate version of the outer catheter shown in FIG. 10, shown with dashed lines representing otherwise unseen internal features, in accordance with the invention.
Figure 12:
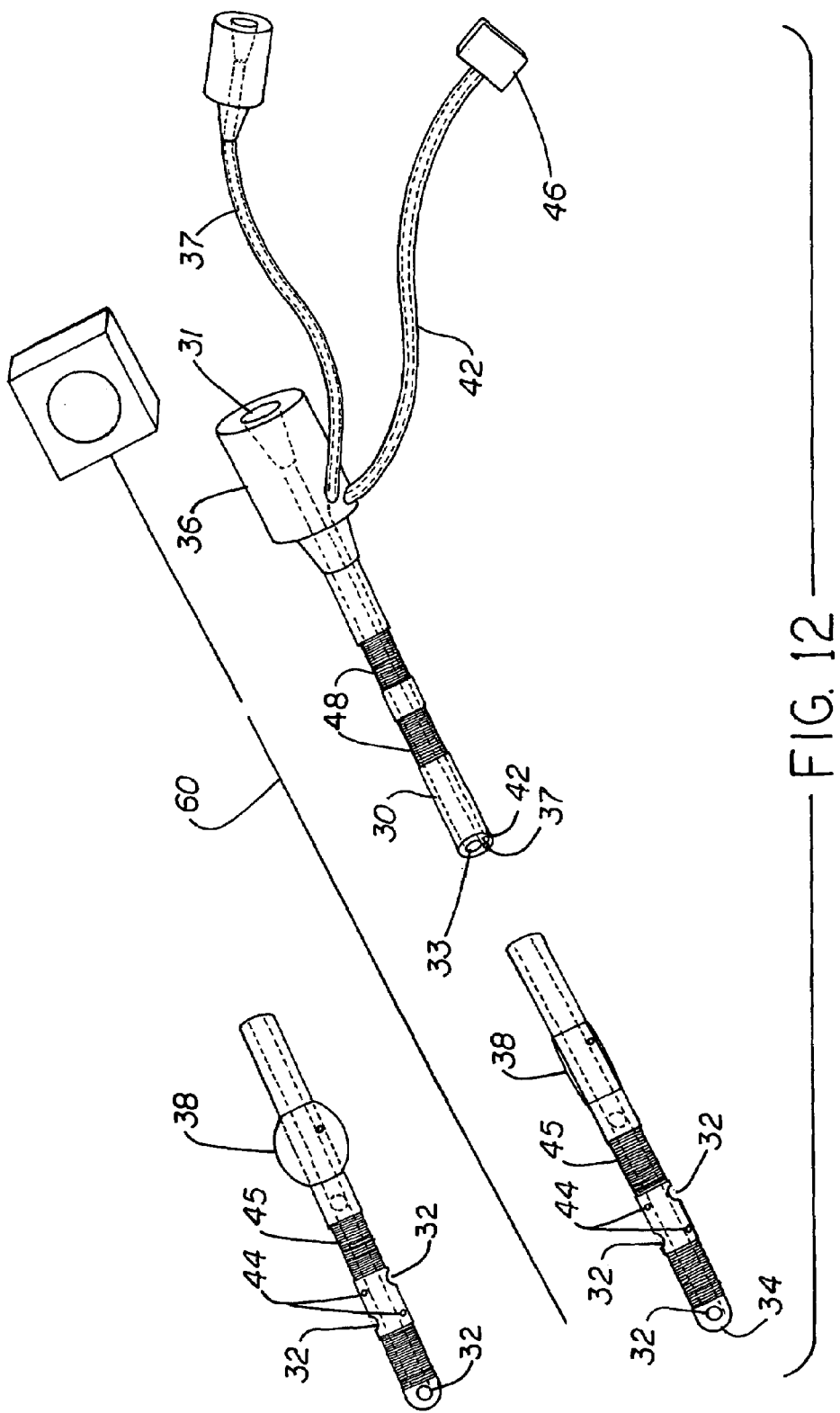
FIG. 12 is a perspective view of an alternate version of the outer catheter shown in FIGS. 10 and 11, shown with dashed lines representing otherwise unseen internal features, in accordance with the invention.
Figure 13:
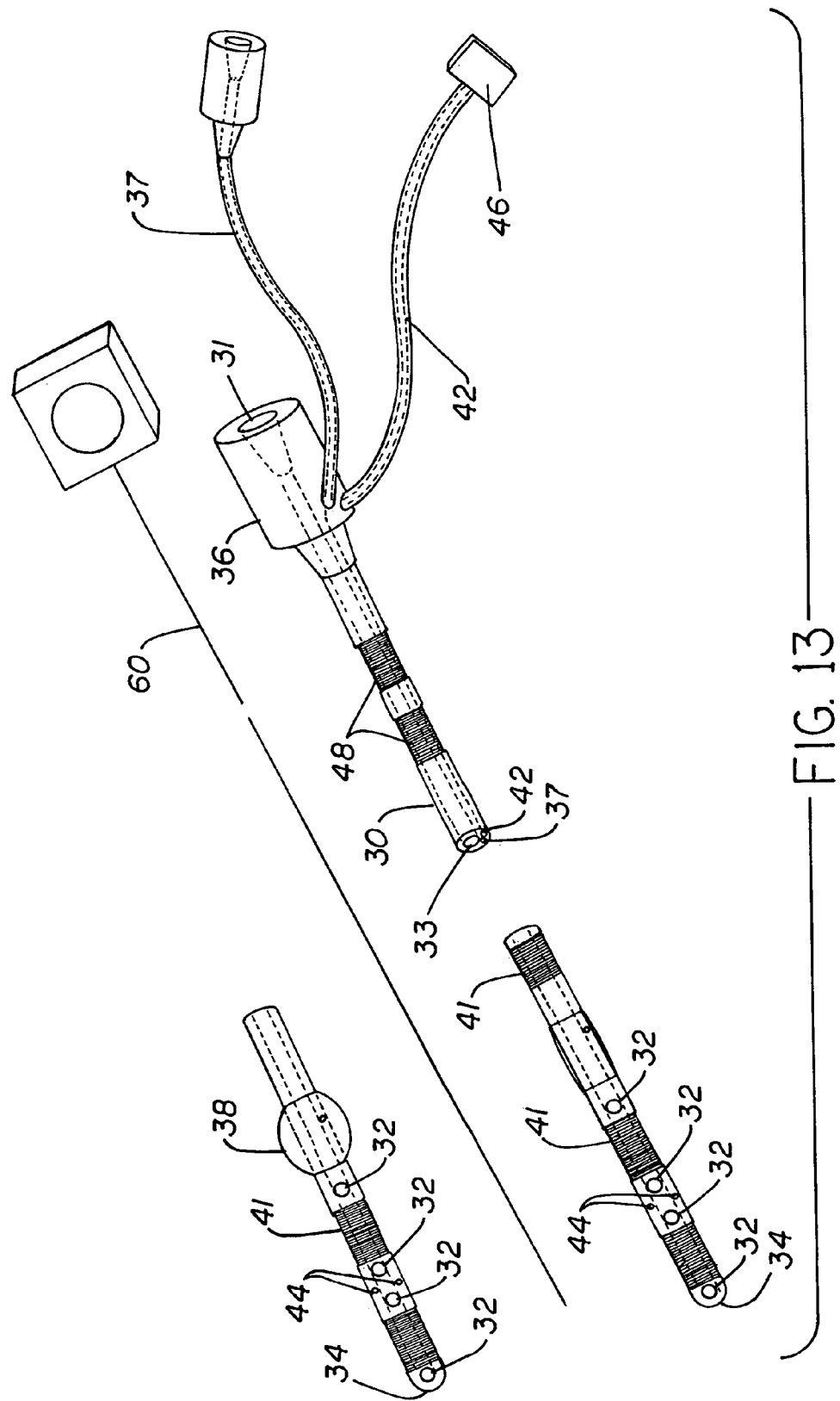
FIG. 13 is a perspective view of an alternate version of the outer catheter shown in FIGS. 10–12, shown with dashed lines representing otherwise unseen internal features, in accordance with the invention.

FIGS. 6–14d pertain to a preferred embodiment of the catheter assembly 10 in which outer catheter 30 includes an inflatable balloon 38. As shown in FIG. 6, a conduit 37 leads to balloon 38 to provide for the introduction of a fluid to inflate balloon 38 and, if necessary to withdraw fluid from balloon 38 to cause deflation (in certain embodiments fluid permeates through balloon 38 to treat the tissue region surrounding balloon 38). As shown, conduit 37 terminates at a plug which can be connected to another device to receive or dispense fluid. Conduit 37 runs alongside lumen 33 and terminates at balloon 38. FIGS. 6–8 show the alternate embodiments in which apertures 32 are variously positioned as discussed above. In each of FIGS. 6–8 elements 40 are distal contacts 41, and more specifically are macro contacts of the collar-type which circumscribe outer catheter 30. Proximal contacts 48 connect to distal contacts 41 to communication brain activity from distal contacts 41 to a recording or analysis instrument. Proximal contacts 48 do not enter the patient's brain, instead they provide connection to such an instrument.

Balloon 38 can be inflated to block any insertion tract created when catheter assembly 10 is inserted into the brain such that any drug administered to the brain cannot migrate through any tract. In addition, balloon 38 may be inflated with a drug or other fluid which is intended to be administered to the brain. In this manner, fluids may be transferred between the brain and the apertures 32 at the same time fluids are introduced to the brain through balloon 38 through permeation. Balloon 38 is particularly adept at administering fluids to the brain slowly over a period of time which may allow for effective introduction of the fluid to the brain.

FIGS. 9a, 9b, 9c and 9d differ from FIGS. 6–8 in that outer catheter 30 includes a distal portion which has a reduced diameter. Such an embodiment provides for minimized invasiveness at the targeted tissue region. FIGS. 9b, 9c and 9d are enlarged views of the distal portion about which apertures 32 may be variously positioned.

Figure 14A:
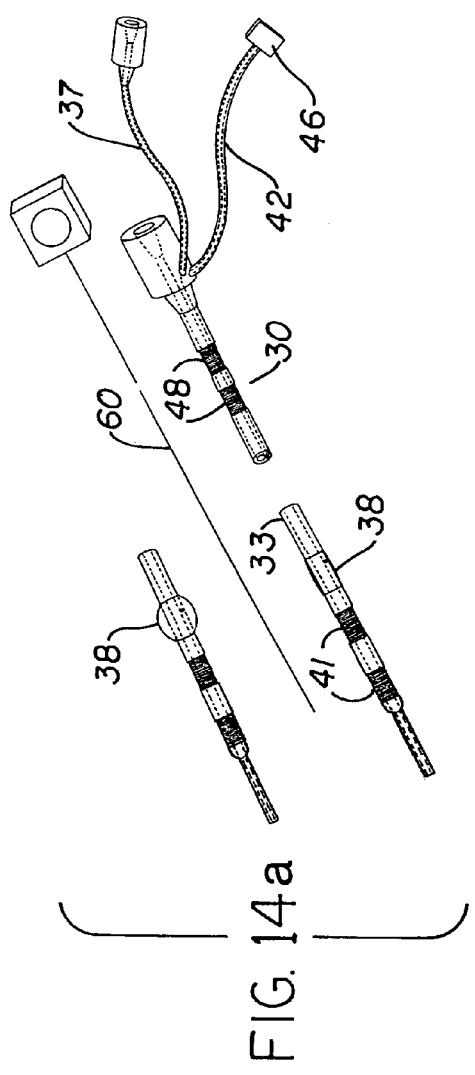
FIGS. 14*a*, 14*b*, 14*c* and 14*d* are perspective views of alternate versions of the outer catheters shown in FIGS. 10–13, shown with dashed lines representing otherwise unseen internal features, in accordance with the invention.
Figure 14B:
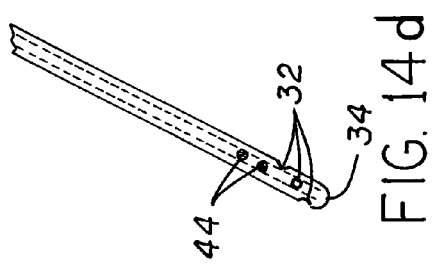
Figure 14C:
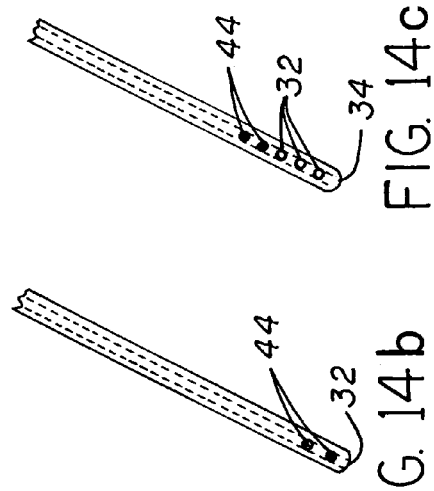
Figure 14D:
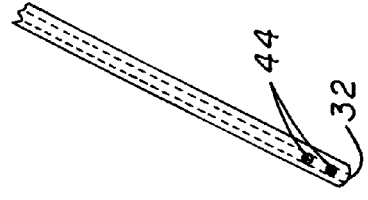

FIGS. 10–14d depict an outer catheter 30 which includes micro contacts 44 and/or macro contacts 45 and a lead 42 which communicates brain activity through connector 46. As shown, lead 42 runs alongside conduit 37 and lumen 33 to distal contacts 41 (micro contacts 44 and/or macro contacts 45). It is noted that sensing contacts 41 may be positioned on both the distal and proximal sides of balloon 38. Such a design allows for monitoring of brain tissue which is being treated with drugs simultaneous with monitoring of brain tissue which is not being treated. Micro contacts 44 and apertures 32 are shown variously positioned in FIGS. 10–14d as apertures 32 were shown and discussed as being variously positioned above. For example, FIGS. 14b, 14c and 14d show the distal portions of outer catheter 30 and have an axially aligned aperture 32 and axially spaced micro contacts 44 in a line parallel to lumen 33 (FIG. 14b), micro contacts 44 and apertures 32 axially spaced in a line parallel to lumen 33 (FIG. 14c) and radially and axially spaced apertures 32 and axially spaced micro contacts 44 (FIG. 14d).

Figure 16:
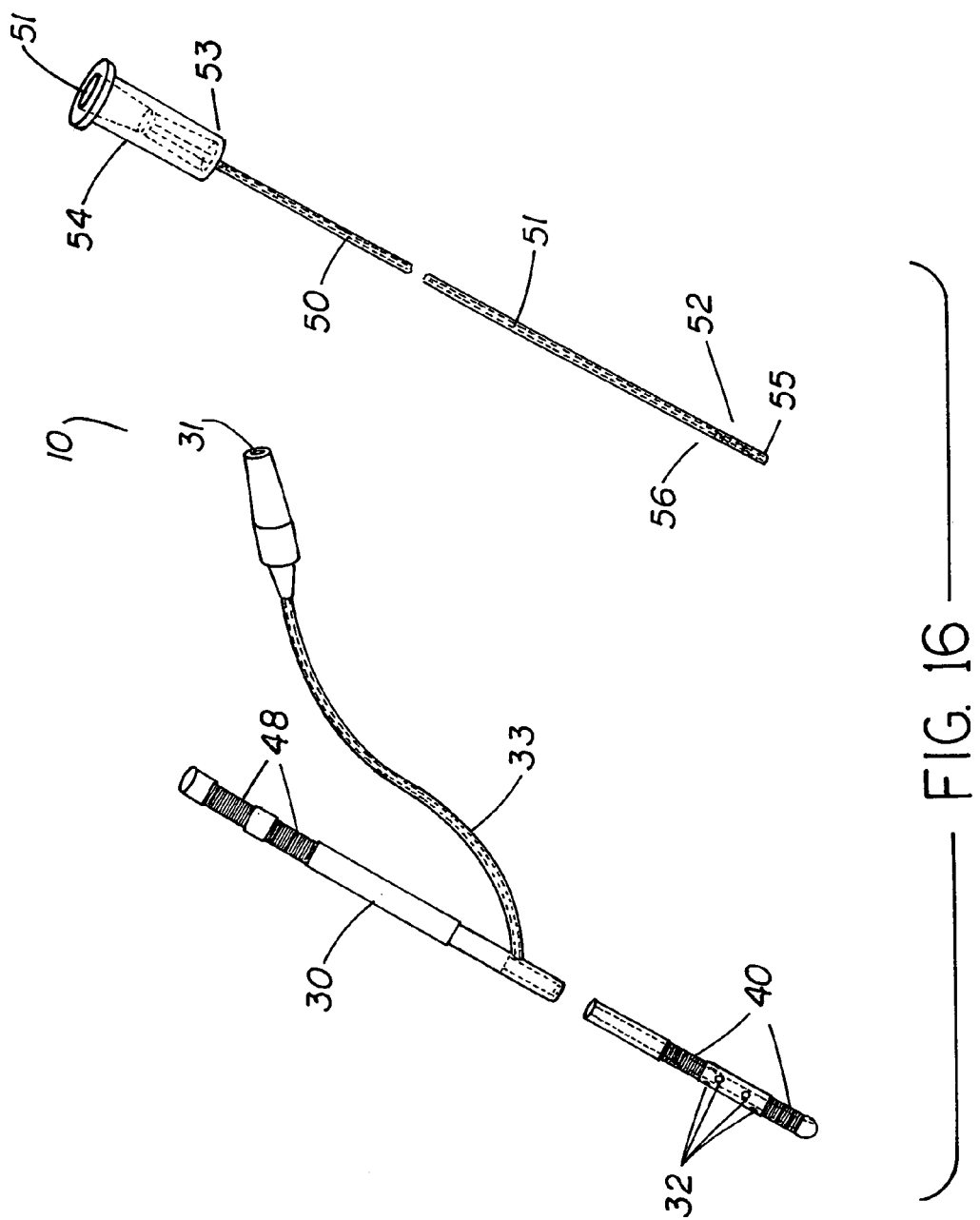

FIGS. 15 and 16 depict a catheter assembly 10 which includes a inner catheter 50 with a port 52 which is a micro dialysis membrane 55. In such an embodiment, outer catheter 30 includes apertures 32 which allow cerebral spinal fluid to reach membrane 55. Fluid moves through membrane 55 and is transferred through passageway 51 to external receptacles or analysis devices. In FIG. 15, proximal opening 31 is axially aligned with outer catheter 30 such that lumen 33 passes through proximal contacts 48. In FIG. 16, lumen 33 branches off of outer catheter 30 through a flexible tubing before reaching proximal contacts 48 (proximal contacts 48 are connected to distal contacts 41 by an unshown connection). Inner catheter is received in lumen 33 and moves into outer catheter 30 to ports 32. In such an embodiment, inner catheter is sufficiently flexible to navigate lumen 33.

Figure 17A:
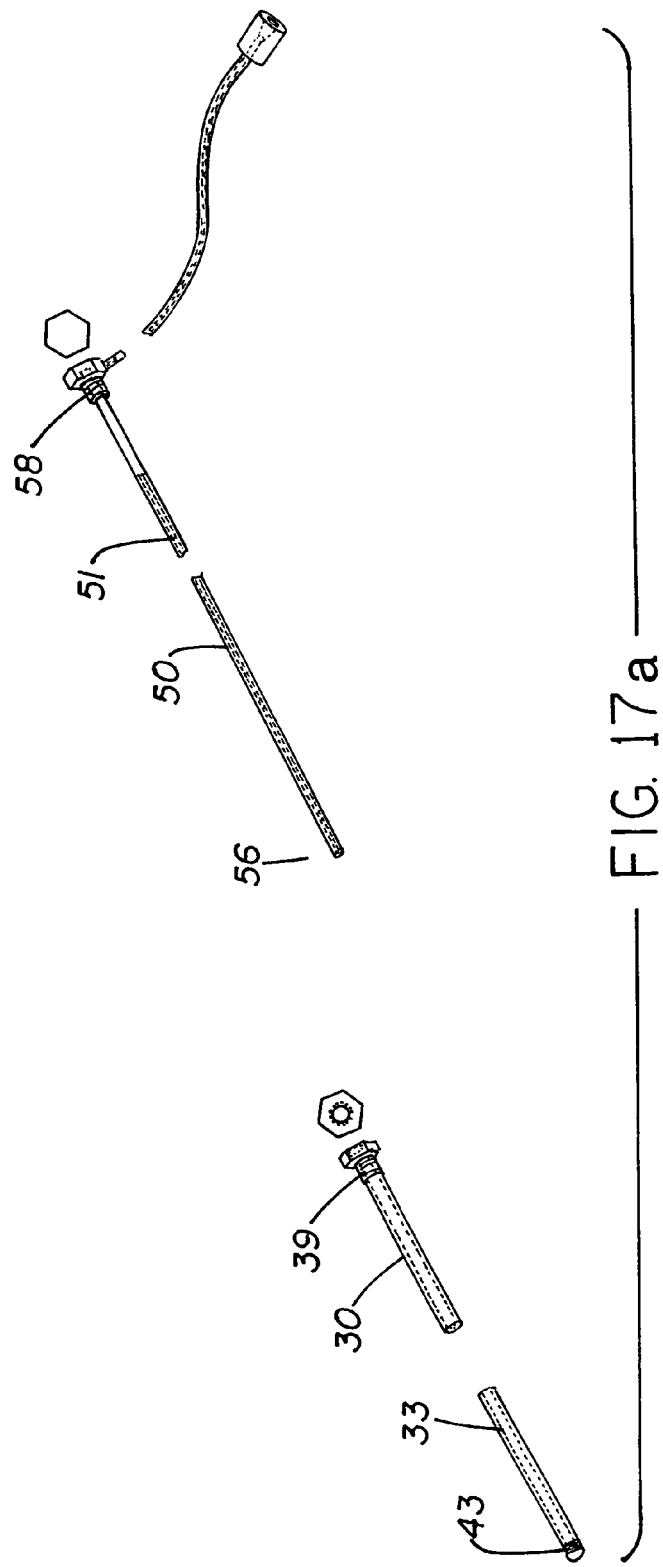

FIG. 17a shows catheter assembly 10 including an outer catheter 30 which has a location marker 43 as element 40. Location marker 43 is preferably comprised of a material which contains a mobile phase suitable for MRI imaging by commercial machines, and which is sufficiently X-Ray-opaque for adequate imaging on CT or X-ray. Catheters 30,50 also include threads 39,58 which provide for attachment to the patient's brain and between the catheters 30,50. Such an outer catheter 30 can be called a trajectory catheter when used in this manner. In a preferred method of use, trajectory catheter 30 is inserted into the brain and positioned at a desired location in the brain by using marker 43. Outer catheter 30 is then connected to the patient's skull by screwing threads 39 into the skull. Then inner catheter 50 is inserted through lumen 33 and connected to outer catheter 30 by threads 58.

FIG. 17b shows the distal portions 56 of a set 59 of inner catheters including ports 52 which are variously positioned on distal portions 56 as shown. In certain preferred embodiments, inner catheters 50 of different lengths, such as those shown, are supplied with an outer catheter 30 such that, after inserting outer catheter 30 into the patient's brain, an inner catheter 50 of a specific length is selected to treat a desired tissue region at a known location beyond outer catheter 30. After treatment at that location, the inner catheter 50 can be removed and another inner catheter 50 of a different length and/or different port arrangement can be inserted into the patient's brain to treat a different desired tissue region. For instance, an inner catheter 50 which extends 0.5 cm beyond outer catheter 30 may be used to treat the tissue region 0.5 cm beyond outer catheter 30 and then removed from lumen 33 before another inner catheter 50 which extends 2.0 cm beyond outer catheter 30 is inserted through lumen 33 and used to treat the tissue region 2.0 cm beyond outer catheter 30. A set of inner catheters 50 is preferably provided with an outer catheter 30 such that a physician may select specific inner catheters 50 to treat the desired tissue regions. Such a set allows for specific treatment of different tissue regions, such as those found in and around tumors, with the same or different drugs without requiring multiple insertions through the intervening brain tissue.

In some embodiments, outer catheter has apertures on its side (not shown) which correspond to ports 52. In other embodiments, outer catheter has only a open ended lumen 33 such that the aperture is aligned with lumen 33, and inner catheter 50 includes ports 52 on its distal portion which extends out of lumen 33 when inserted into the patient's brain. Outer catheter 30 can further include contacts 41 as disclosed in the prior figures.

While the invention has been described with respect to specific embodiments by way of illustration, many modifications and changes will occur to those skilled in the art. It is, therefore, to be understood that the appended claims are intended to cover all such modifications and changes as fall within the true scope and spirit of the invention.

The invention claimed is:

1. A method of treating a tissue region in the brain of a patient comprising:
  inserting into the brain an outer catheter having an exterior surface, an inflatable balloon mounted upon the exterior surface, at least one element distal to the balloon, at least one aperture and a lumen, the element being adapted to monitor brain activity within the tissue region, to electronically stimulate the tissue region, or to provide information on a precise position of the element when the element is located entirely within the brain and being mounted proximal to a distal end of the outer catheter upon an exterior surface of a distal portion of the outer catheter;

inflating the balloon to seal a tract created during insertion of the outer catheter into the brain;

inserting into the lumen an inner catheter having a passageway extending between a proximal end and at least one port, the outer catheter guiding the inner catheter to the tissue region; and transferring fluids between the tissue region and the proximal end through the passageway.

2. The method of claim 1 wherein a stylet is positioned in the lumen during insertion of the outer catheter into the brain and further comprising removing the stylet from the outer catheter before the inner catheter is inserted into the lumen.

3. The method of claim 2 further comprising connecting the outer catheter to the patient's skull and connecting the inner catheter to the outer catheter.

4. The method of claim 1 wherein the element is a location marker and further including locating the position of the location marker within the brain by utilizing magnetic resonance imaging.

5. The method of claim 1 wherein the element is a location marker and further including locating the position of the location marker within the brain by utilizing computerized x-ray tomography.

6. The method of claim 1 wherein the outer catheter includes a tapered fitting at a proximal end of the lumen, the fitting engaging the inner catheter upon insertion into the lumen so that unintended relative movement between the outer catheter and inner catheter is prevented.

7. The method of claim 1 wherein the inner catheter has a distal end which passes through the aperture into the tissue region beyond the outer catheter during the insertion of the inner catheter into the lumen.

8. The method of claim 1 wherein the inner catheter has a distal end and the outer catheter has a closed lumen so that the distal end is contained within the outer catheter when the inner catheter is inserted into the lumen.

9. The method of claim 1 wherein the transferring action includes delivering drugs to the tissue region through the at least one port.

10. The method of claim 1 wherein the transferring action includes withdrawing cerebral spinal fluid through the at least one port.

11. The method of claim 10 wherein the inner catheter includes a micro-dialysis membrane at the at least one port, the cerebral spinal fluid passing through the membrane during the withdrawing action.

12. The method of claim 1 wherein the balloon is inflated with a drug and further comprising delivering the drug to the tissue region through the balloon.

13. The meted of claim 12 further comprising delivering a second drug to the tissue region through the at least one port.

14. The method of claim 1 wherein the element monitors brain activity and further comprising sensing chemical changes at the tissue region via the element.

15. The method of claim 1 wherein the element monitors brain activity and further comprising sensing electrical changes at the tissue region via the element.

16. The method of claim 1 wherein the element is a fiber optic contact.

17. A method of treating a tissue region in the brain of a patient comprising:

inserting into the brain an outer catheter having at least one element adapted to monitor brain activity within the tissue region, to electronically stimulate the tissue region, or to provide information on a precise position of the element when the element is located entirely within the brain, at least one aperture and a lumen;

inserting into the lumen an inner catheter having a passageway extending between a proximal end and at least one port, the lumen snugly receiving the inner catheter and guiding the inner catheter to the tissue region and the outer catheter including a tapered fitting at a proximal end of the lumen, the fitting being adapted to be frictionally received by the inner catheter upon non-radial and substantially axial insertion of the inner catheter into the lumen and to be engaged by the inner catheter following insertion so that unintended relative movement between the outer catheter and inner catheter upon engagement is avoided; and transferring between the tissue region and the proximal end fluids filling the passageway.

18. A method of treating a tissue region in the brain of a patient comprising:

inserting into the brain an outer catheter having at least one element adapted to monitor brain activity within the tissue region or to electronically stimulate the tissue region, an inflatable balloon proximal to the at least one element and mounted upon an exterior surface of the outer catheter, at least one aperture and a lumen;

sensing or stimulating brain activity in the tissue region via the element;

inserting into the lumen an inner catheter having a passageway extending between a proximal end and at least one port, the outer catheter guiding the inner catheter to the tissue region; and transferring fluids between the tissue region and the proximal end through the passageway.

19. The method of claim 18 further comprising the step of inflating the balloon to seal a tract created during insertion of the assembly into the brain.

20. The method of claim 19 wherein the tissue region is distal to the balloon along the tract and the fluids are drugs being delivered to the tissue region through the port such that the at least one element distal to the balloon is sensing and stimulating brain activity in the tissue region treated with the drugs.

* * * * *

UNITED STATES PATENT AND TRADEMARK OFFICE
CERTIFICATE OF CORRECTION

| | | |
|---|---|---|
| PATENT NO. | : 7,241,283 B2 | Page 1 of 1 |
| APPLICATION NO. | : 10/423587 | |
| DATED | : July 10, 2007 | |
| INVENTOR(S) | : David A. Putz | |

It is certified that error appears in the above-identified patent and that said Letters Patent is hereby corrected as shown below:

On The Title page, Item (57) ABSTRACT, line 14, after "element" delete "catheter".

Signed and Sealed this

Twenty-third Day of October, 2007

JON W. DUDAS
*Director of the United States Patent and Trademark Office*